United States Patent [19]

Sakano et al.

[11] Patent Number: 4,532,137
[45] Date of Patent: Jul. 30, 1985

[54] 2-THIAZOLAMINE DERIVATIVES, PROCESS FOR PREPARING SAME, AND PHARMACEUTICAL COMPOSITIONS COMPRISING SAME

[75] Inventors: Isao Sakano; Tatsuro Yokoyama; Seitaro Kajiya, all of Yokohama; Yutaka Okazaki, Mobara; Hiroshi Tokuda, Mobara; Hiroshi Kawazura, Mobara; Mikio Kumakura, Mobara; Takuo Nakano, Yokohama; Akira Awaya, Yokohama, all of Japan

[73] Assignee: Mitsui Toatsu Chemicals, Incorporated, Tokyo, Japan

[21] Appl. No.: 568,826

[22] Filed: Jan. 6, 1984

Related U.S. Application Data

[62] Division of Ser. No. 438,851, Oct. 22, 1982, Pat. No. 4,473,577.

[30] Foreign Application Priority Data

Mar. 16, 1981 [JP] Japan ................................. 56-36521

[51] Int. Cl.³ .................. C07D 277/48; A61K 31/425
[52] U.S. Cl. .................................................. 514/371
[58] Field of Search ........................ 548/195; 424/270

[56] References Cited

U.S. PATENT DOCUMENTS

| | | | | |
|---|---|---|---|---|
| 4,203,899 | 5/1980 | Ochiai | ................................ | 548/194 |
| 4,279,818 | 7/1981 | Takaya | ................................ | 424/246 |
| 4,304,770 | 12/1981 | Takaya | ................................ | 424/246 |
| 4,313,945 | 2/1982 | Wiederkehr | ........................ | 424/246 |

*Primary Examiner*—Robert Gerstl
*Attorney, Agent, or Firm*—Fisher, Christen & Sabol

[57] ABSTRACT

Disclosed are 2-thiazol derivatives having the general formula

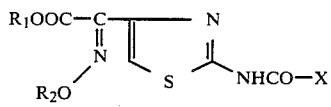

where $R_1$ and $R_2$ independently represent lower alkyl radicals having 1 to 4 carbon atoms and X represents a lower alkyl radical, a lower alkoxy radical, a lower alkoxycarbonyl radical, a halogenoalkoxy radical, a radical of the formula

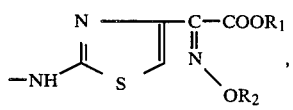

or a radical of the formula

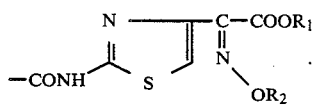

Also disclosed are a process for preparing the derivatives and pharmaceutical compositions having immunomodulatory activity which comprise the derivatives as the active ingredient.

6 Claims, No Drawings

2-THIAZOLAMINE DERIVATIVES, PROCESS FOR PREPARING SAME, AND PHARMACEUTICAL COMPOSITIONS COMPRISING SAME

DESCRIPTION

This is a division of application Ser. No. 438,851, filed Oct. 22, 1982, now U.S. Pat. No. 4,473,577.

TECHNICAL FIELD

This invention relates to novel 2-thiazolamine derivatives, a process for preparing the same, and pharmaceutical compositions comprising the same. More particularly, it relates to novel 2-thiazolamine derivatives which have such immunomodulatory activity as to make them effective against immune diseases (e.g., rheumatoid arthritis) and also useful in the treatment of viral diseases and in the immunotherapy of cancer and, moreover, are very desirable for therapeutic purposes because of their low toxicity, a process for preparing the same, and pharmaceutical compositions comprising the same.

BACKGROUND ART

Conventionally, a large number of steroidal and non-steroidal anti-inflammatory agents have been used in the clinical treatment of autoimmune diseases such as rheumatism and the like. However, these numerous drugs are still not entirely satisfactory, judging from their pharmacological actions, side effects, toxicity, and the like.

DISCLOSURE OF THE INVENTION

It is an object of the present invention to provide a novel 2-thiazolamine derivative which exerts a specific effect on the cells participating in immune responses and thereby serves to modify the immune responses of the host, and a process for preparing this compound.

It is another object of the present invention to provide a pharmaceutical composition characterized by immunomodulatory activity and low toxicity.

In accordance with one feature of the present invention, there is provided a 2-thiazolamine derivative having the general formula

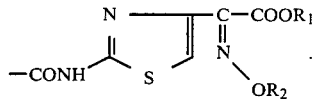  (1)

where $R_1$ and $R_2$ independently represent lower alkyl radicals having 1 to 4 carbon atoms and X represents a lower alkyl radical, a lower alkoxy radical, a lower alkoxycarbonyl radical, a halogenoalkoxy radical, a radical of the formula

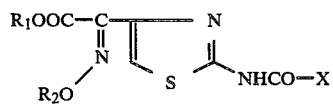

or a radical of the formula

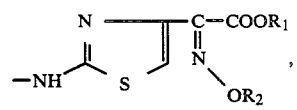

In accordance with another feature of the present invention, compounds of the general formula (1) can be prepared by reacting a 2-(2-aminothiazol-4-yl)-2-syn-oxyiminoacetic acid ester of the general formula

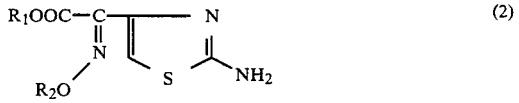  (2)

where $R_1$ and $R_2$ are as defined for the general formula (1), with a compound of the general formula

A—CO—B  (3)

where A represents a halogen atom or a lower alkoxy radical and B represents a halogen atom, a lower alkyl radical, a lower alkoxy radical, a halogenoalkoxy radical, or a radical of the formula —CO—A.

In accordance with still another feature of the present invention, a pharmaceutical composition having immunomodulatory activity comprises a compound of the general formula (1) and a pharmaceutically acceptable carrier.

BEST MODE FOR CARRYING OUT THE INVENTION

Specific examples of the 2-thiazolamine derivatives represented by the general formula (1) include 2-[(2-acetylamino)thiazol-4-yl]-2-syn-methoxyiminoacetic acid methyl ester, 2-[(2-propionylamino)thiazol-4-yl]-2-syn-methoxyiminoacetic acid methyl ester, 2-[(2-propionylamino)thiazol-4-yl]-2-syn-methoxyiminoacetic acid ethyl ester, 2-[(2-propionylamino)thiazol-4-yl]-2-syn-ethoxyiminoacetic acid ethyl ester, 2-[(2-propionylamino)thiazol-4-yl]-2-syn-ethoxyiminoacetic acid methyl ester, 2-[(2-n-butyrylamino)thiazol-4-yl]-2-syn-methoxyiminoacetic acid methyl ester, 2-[(2-isobutyrylamino)thiazol-4-yl]-2-syn-methoxyiminoacetic acid methyl ester, 2-[(2-n-pentanoylamino)thiazol-4-yl]-2-syn-methoxyiminoacetic acid methyl ester, 2-[2-(α-methylbutyryl)amino)thiazol-4-yl]-2-syn-methoxyiminoacetic acid methyl ester, 2-[(2-(β-methylbutyryl)amino)thiazol-4-yl]-2-syn-methoxyiminoacetic acid methyl ester, 2-[(2-(α,α-dimethylpropionyl)amino)thiazol-4-yl]-2-syn-methoxyiminoacetic acid methyl ester, 2-[(2-methoxycarbonylamino)thiazol-4-yl]-2-syn-methoxyiminoacetic acid methyl ester, 2-[(2-ethoxycarbonylamino)thiazol-4-yl]-2-syn-methoxyiminoacetic acid methyl ester, 2-[(2-β,β,β-trichloroethoxycarbonylamino)thiazol-4-yl]-2-syn-methoxyiminoacetic acid methyl ester, 2-[(2-β-chloroethoxycarbonylamino)thiazol-4-yl]-2-syn-methoxyiminoacetic acid methyl ester, 2-[(2-β-bromoethoxycarbonylamino)thiazol-4-yl]-2-syn-methoxyiminoacetic acid methyl ester, 2-[(2-ethoxycarbonylamino)thiazol-4-yl]-2-syn-methoxyiminoacetic acid ethyl ester, 2-[(2-n-propoxycarbonylamino)thiazol-4-yl]-2-syn-methoxyiminoacetic acid methyl ester, 2-[(2-isopropoxycarbonylamino)thiazol-4-yl]-2-syn-methoxyiminoacetic acid methyl ester, 2-[(2-n-butoxycarbonylamino)- thiazol-4-yl]-2-syn-methoxyiminoacetic acid methyl ester, 2-[(2-isobutoxycarbonylamino)thiazol-4-yl]-2-syn-methoxyiminoacetic acid methyl ester, N-[4-syn-(carbomethoxy methoxyiminomethyl)thiazol-2-yl]oxamic acid methyl ester, N-[4-syn-(carbomethoxy methoxyiminomethyl)thiazol-2-yl]oxamic acid ethyl ester, N-[4-syn-(carboethoxy methoxyiminomethyl)thiazol-2-yl]oxamic acid ethyl ester, N-[4-syn-(carbomethoxy methoxyiminomethyl)thiazol-2-yl]oxamic acid n-propyl ester, N-[4-syn-(carbomethoxy methoxyiminomethyl)thiazol-2-yl]oxamic acid isopropyl ester, N-[4-syn-(carbomethoxy methoxyiminomethyl)thiazol-2-yl-]oxamic acid n-butyl ester, N-[4-syn-(carbomethoxy methoxyiminomethyl)thiazol-2-yl]oxamic acid isobutyl ester, N-[4-syn-(carbomethoxy methoxyiminomethyl)thiazol-2-yl]oxamic acid tert-butyl ester, N,N'-bis[4-syn-(carbomethoxy methoxyiminomethyl)thiazol-2-yl]urea, N,N'-bis[4-syn-(carboethoxy methoxyiminomethyl)thiazol-2-yl]urea, N,N'-bis[4-syn-(carboethoxy ethoxyiminomethyl)thiazol-2-yl]urea, N,N'-bis[4-syn-(carbomethoxy methoxyiminomethyl)thiazol-2-yl]oxamide, N,N'-bis[4-syn-(carboethoxy methoxyiminomethyl)thiazol-2-yl]oxamide, and N,N'-bis[4-syn-(carboethoxy ethoxyiminomethyl)thiazol-2-yl]oxamide.

In preparing such 2-thiazolamine derivatives according to the process of the present invention, the reaction is preferably carried out by dissolving or suspending a starting material of the general formula (2) (which may be present in the form of a salt formed by the addition of a suitable acid) and adding thereto a compound of the general formula (3), for example, drop by drop. Preferred example of the compounds represented by the general formula (3) include acetyl chloride, propionyl chloride, chloroformic acid ethyl ester, ethylaxalyl chloride, phosgene, oxalyl chloride, diethyl carbonate, diethyl oxalate, tert-butyl ethyl oxalate, and the like. Specific examples of the solvents suitable for this purpose include benzene, toluene, xylene, acetone, ethyl methyl ketone, dioxane, pyridine, N,N-dimethylformamide, methylene chloride, chloroform, carbon tetrachloride, 1,1-dimethoxyethane, tetrahydrofuran, and the like. Depending on the type of the reaction, it may be beneficial to use an organic base (such as pyridine or triethylamine) or an inorganic base (such as sodium hydrogencarbonate, sodium carbonate, or potassium carbonate) for the purpose of removing the acid formed during the reaction.

Although the above-described reaction proceeds even at room temperature or below, the reaction mixture may be heated up to the boiling point of the solvent in order to accelerate the reaction.

2-(2-Aminothiazol-4-yl)-2-syn-oxyiminoacetic acid esters of the general formula (2), which are used as starting materials in the process of the present invention, can be prepared according to the method described, for example, in Japanese Patent Laid-Open No. 101393/'78.

The compounds of the present invention, which are within the scope of the above general formula (1), have pharmacological activities. Among others, the present inventor has unexpectedly found that the compounds of the present invention have immunomodulatory activity.

Moreover, the compounds of the present invention are very useful for therapeutic purposes because of their low toxicity.

These facts are more fully explained with reference to the following evaluation tests.

A variety of experimental systems are being commonly used to test immunomodulatory activity in animals. Of such tests, the most typical one is an augmentation test of delayed hypersensitivity as shown below.

The delayed hypersensitivity induced in mice by applying picryl chloride(2-chloro-1,3,5-trinitrobenzene) to the skin is known to be a typical phenomenon of cellular immunity and constitutes one of the experimental systems in world-wise use (Asherson, G. L., and Ptak, W. "Contact and delayed hypersensitivity in the mouse I. Active sensitization and passive transfer," Immunology, 15, 405–416(1968)).

In the following Evaluation Test 1, this experimental system was used to carry out an augmentation test of delayed hypersensitivity.

EVALUATION TEST 1 [AUGMENTATION TEST OF DELAYED HYPERSENSITIVITY]

Test procedure:

Male mice of the ICR strain, weighing approximately 30 g, were used in groups of eight. These animals were sensitized by shaving the hair on the abdomen and applying thereto a 3% solution of picryl chloride in a 4:1 mixture of olive oil and acetone. Simultaneously with this sensitization, each of three compounds of the present invention was dissolved or suspended in physiological saline containing 0.2% carboxymethyl cellulose and administered orally to the animals in a dose of 50 mg per kg of body weight. A control group was treated solely with physiological saline containing 0.2% carboxymethyl cellulose.

Seven days after sensitization, the animals were challenged by wrapping the tips of a forceps with pieces of felt, impregnating the felt with olive oil containing 1% picryl chloride, and pinching both ears of each animal. The thicknesses of the ears were measured before and 24 hours after the challenge, and the calculated percent increase of ear thickness (the average of 16 measurements made of the ears of 8-animals) is shown in Table 1. For purposes of comparison, the results of an experiment with Levamisole hydrochloride are also given. The test results thus obtained were subjected to statistical analysis using the F.t test. The values marked with an asterisk (*) indicate that, when they were compared with the value of the control, the differences were significant at $P < 0.05$.

Results:

By administering the compounds of the present invention simultaneously with sensitization, the reaction evoked by a challenge was augmented. The activity of the compounds of the present invention was found to be equal to or higher than that of Levamisole used for comparative purposes. Thus, the compounds of the present invention are considered to have the capacity to modulate cellular immune responses in mice (i.e., immunomodulatory activity).

TABLE 1

Test for Augmentation of Delayed Hypersensitivity

| Compound | Percent increase of ear thickness |
|---|---|
| H₃COOC—C(=N-N(H₃CO))—S—C(=N)—NHCOOCH₂CCl₃ | 33.4* |
| H₃COOC—C(=N-N(H₃CO))—S—C(=N)—NHCH(=O)—N—S—C(COOCH₃)=N(OCH₃) | 30.3 |
| H₃COOC—C(=N-N(H₃CO))—S—C(=N)—NHCOC₂H₅ | 35.2* |
| Levamisole hydrochloride | 31.2* |

The adjuvant arthritis induced in rats by injection of a tubercle bacillus adjuvant is frequently used as an experimental model for rheumatoid arthritis in man.

Although the mechanism by which this phenomenon occurs is not completely elucidated, cellular immunity is known to play an important role. Using this well-known adjuvant arthritis test, the same compounds of the present invention were further examined for immunomudulatory activity.

EVALUATION TEST 2 [ADJUVANT ARTHRITIS TEST (TABLE 2)]

Test Procedure:

An adjuvant was prepared by suspending 0.4 mg of killed and dried cells of the human type tubercle bacillus (Mycobacterium tuberculosis) in 0.1 ml of liquid paraffin, and inoculated intradermally into the sole of the right hind paw of 8-weeks-old male rats of the SD strain. Each of the three compounds of the present invention was subcutaneously administered nine times before and after injection of the adjuvant. These compounds were dissolved or suspended in physiological saline containing 0.2% carboxymethyl cellulose and administered in an amount of 5 mg per kg of body weight. The volume of the left hind paw of each animal was measured daily from the day of inoculation of the adjuvant to the end of the test, and the percent inhibition of swelling was calculated. For purposes of comparison, the results of an experiment with Levamisole hydrochloride are also given. The test results thus obtained were subjected to statistical analysis using the F.t test. The values marked with an asterisk (*) indicate that, when they were compared with the value of a control group treated solely with physiological saline containing 0.2% carboxymethyl cellulose, the differences were significant at $P<0.05$.

Results:

The compounds of the present invention remarkably inhibited secondary inflammation of the adjuvant arthritis and their effect was statistically significant as compared with the control group. The activity of the compounds of the present invention was found to be equal to or higher than that of Levamisole used for comparative purposes. Thus, the compounds of the present invention are considered to have immunomodulatory activity and, in addition, an antiarthritic effect.

TABLE 2

Adjuvant Arthritis Tests

| Compound | Number of animals | Percent inhibition of swelling as compared with control group (average of 16–20 days) |
|---|---|---|
| H₃COOC—C(=N-N(H₃CO))—S—C(=N)—NHCOOCH₂CCl₃ | 10 | 39.5* |
| H₃COOC—C(=N-N(H₃CO))—S—C(=N)—NHCH(=O)—N—S—C(COOCH₃)=N(OCH₃) | 10 | 34.5* |

TABLE 2-continued

Adjuvant Arthritis Tests

| Compound | Number of animals | Percent inhibition of swelling as compared with control group (average of 16–20 days) |
|---|---|---|
| H₃COOC—C(=N—N(OCH₃))—[thiazole-S]—C(=O)NHCOC₂H₅ | 10 | 22.3 |
| Levamisole hydrochloride | 44 | 19.8* |

As can be seen from Evaluation Tests 1 and 2, the compounds of the present invention have strong immunomodulatory activity. Accordingly, they are effective in the treatment of diseases which are known to involve impairments of or abnormalities in immunological function, for example, autoimmune diseases such as rheumatoid arthritis and the like.

The toxicity of the active ingredients of some typical pharmaceutical compositions of the present invention was examined in the following Evaluation Test 3.

EVALUATION TEST 3 [TEST FOR ACUTE ORAL TOXICITY]

Test procedure:

Each of the three compounds used in Evaluation Tests 1 and 2 was dissolved or suspended in physiological saline and administered orally to a group of 5 male mice of the ddY strain. The $LD_{50}$ value of the compound was estimated by observing these animals for 7 days after administration.

Results:

The $LD_{50}$ values of the above compounds were estimated to be not less than 1000 mg/kg. These values are far higher than the estimated $LD_{50}$ value($=200-300$ mg/kg) of Levamisole hydrochloride, so that the active ingredients of the pharmaceutical compositions of the present invention are considered to have sufficiently low toxicity.

As raw materials for the manufacture of pharmaceutical preparations, the compounds of the present invention may be directly used in the form of the free bases. If desired, they may also be used in the form of pharmaceutically acceptable salts.

The pharmaceutical compositions of the present invention can be used in the same dosage forms and by the same administration methods as conventional immunomodulatory or anticancer agents are. More specifically, for purposes of oral administration, they may be formed into capsules, granules, pills, subtle granules, tablets, syrups, and the like. For purposes of intrarectal administration, they are suitably formed into suppositories. For purposes of injection, they may be formed into subcutaneous, intramuscular, and intravenous injections.

The pharmaceutical compositions of the present invention preferably contain an active ingredient in an amount of approximately 10 to 95%, more preferably 15 to 90%, and are prepared according to per se well-known techniques such as blending, granulation, sugar coating, dissolution, and lyophilization. Where they are intended for oral use, the active ingredient is combined with a solid carrier and suitable pharmaceutic aids are added as desired. Specific examples of the useful carriers include sugars, cellulose preparations, calcium phosphate, and the like and specific examples of the useful pharmaceutic aids include binders, disintegrants (e.g., starch), flow controllers, lubricants, and the like. Moreover, any suitable additives may be incorporated according to the dosage form.

The indications for the pharmaceutical compositions of the present invention include a variety of diseases which are known to involve immunological disorder, and specific examples thereof are autoimmune diseases such as rheumatoid arthritis, multiple myositis, etc., various types of infection, various types of cancer, and the like. The pharmaceutical compositions of the present invention can be expected to normalize the immunological function of patients suffering from such diseases.

It is desirable that the administration method and dosage form of the pharmaceutical composition of the present invention should suitably be determined according to the type of the disease, the condition of the patient, and the like. The daily dose per kilogram of body weight should usually be 0.5 to 100 mg, preferably 1 to 30 mg, for oral administration, 1 to 100 mg for intrarectal administration, 1 to 10 mg for intravenous administration, and 1 to 30 mg for subcutaneous or intramuscular administration. However, it is desirable to modify these doses properly according to the type of the disease, the condition of the patient, and the like. Depending on the type of the disease and the condition of the patient, the therapeutic effects of the active ingredient of the present invention can be enhanced by concomitantly using another drug or drugs as desired. By way of example, chemotherapeutic agents for cancer, such as alkylating agents, metabolic antagonists, and the like, cause the side effect of impairing the immunocompetence of the patient. When used in combination with such a drug, the active ingredient of the present invention can be expected to prevent manifestation of the above-described side effect of the drug and thereby enhance the therepeutic effects synergistically.

The present invention is further illustrated by the following examples.

EXAMPLE 1

A solution was prepared by dissolving 4.3 g of 2-(2-aminothiazol-4-yl)-2-syn-methoxyiminoacetic acid methyl ester in 30 ml of tetrahydrofuran and adding thereto 2.0 g of triethylamine, and its temperature was maintained at 0°–5° C. After 2.72 g of ethyloxalyl chloride was added to the above solution, the resulting reaction mixture was stirred for 1 hour. This reaction mixture was concentrated under reduced pressure and the resulting residue taken up in chloroform was washed with water. The crude product thus obtained was subjected to silica gel column chromatography, in which a yield of 3.1 g of N-[4-syn-(carbomethoxy methoxyiminomethyl)thiazol-2-yl]oxamic acid ethyl ester was obtained by elution with a 20:1 mixture of chloroform and tetrahydrofuran.

Melting point: 142°–143.5° C.
Elemental analysis:

|  | C | H | N | S |
|---|---|---|---|---|
| Calculated value (%) for $C_{10}H_{13}N_3O_6S$ | 41.90 | 4.16 | 13.32 | 10.17 |
| Found value (%) | 41.76 | 4.13 | 13.25 | 10.21 |

NMR spectrum ($\delta_{TMS}^{CDCl_3}$, PPM): 1.40 (3H, t, J=7.0 Hz), 3.92 (3H, s), 4.02 (3H, s), 4.42 (2H, q, J=7.0 Hz), 7.32 (1H, s), 11.0 (1H, br: disappeared when the spectrum was recorded in $D_2O$).

EXAMPLE 2

A solution was prepared by dissolving 2.2 g of 2-(2-aminothiazol-4-yl)-2-syn-methoxyiminoacetic acid methyl ester in 20 ml of pyridine. After 1.4 g of ethyloxalyl chloride was added dropwise to the above solution, the resulting reaction mixture was stirred overnight at room temperature. The reaction product was isolated and purified in the same manner as in Example 1 to obtain a yield of 1.9 g of N-[4-syn-(carbomethoxy methoxyiminomethyl)thiazol-2-yl]oxamic acid ethyl ester.

EXAMPLE 3

A reaction mixture was prepared by adding 2.2 g of 2-(2-aminothiazol-4-yl)-2-syn-methoxyiminoacetic acid methyl ester to 50 ml of diethyl oxalate. This reaction mixture was heated at 100° C. for 12 hours and then concentrated under reduced pressure. Thereafter, the reaction product was purified in the same manner as in Example 1 to obtain a yield of 1.5 g of N-[4-syn-(carbomethoxy methoxyiminomethyl]thiazol-2-yl]oxamic acid ethyl ester.

EXAMPLE 4

The procedure of Example 1 was repeated except that propionyl chloride was used in place of the ethyloxalyl chloride. As a result, there was obtained a 42% yield of 2-[(2-propionylamino)-thiazol-4-yl]-2-syn-methoxyiminoacetic acid methyl ester.

Melting point: 140.5°–141.5° C.
Elemental analysis:

|  | C | H | N | S |
|---|---|---|---|---|
| Calculated value (%) for $C_{10}H_{13}N_3O_4S$ | 44.27 | 4.83 | 15.49 | 11.82 |
| Found value (%) | 44.21 | 5.00 | 15.39 | 11.83 |

NMR spectrum ($\delta_{TMS}^{CDCl_3}$, ppm): 1.10 (3H, t, J=8 Hz), 2.50 (2H, q, J=8 Hz), 3.93 (3H, s), 4.02 (3H, s), 7.12 (1H, s), 10.65 (1H, s: disappeared when the spectrum was recorded in $D_2O$).

EXAMPLE 5

A solution was prepared by dissolving 2.15 g of 2-(2-aminothiazol-4-yl)-2-syn-methoxyiminoacetic acid methyl ester in 40 ml of acetone and adding thereto 1.0 g of sodium hydrogencarbonate, and its temperature was maintained at 0°–5° C. After 1.42 g of chloroformic acid β-chloroethyl ester was added to the above solution, the resulting reaction mixture was stirred at room temperature for 2 hours. This reaction mixture was filtered to remove any inorganic matter, and the filtrate was concentrated under reduced pressure. The resulting residue was subjected to silica gel column chromatography, in which a yield of 2.1 g of 2-[(2-β-chloroethoxycarbonylamino)thiazol-4-yl]-2-syn-methoxyiminoacetic acid methyl ester was obtained by elution with chloroform.

Melting point: 76°–78° C.
Elemental analysis:

|  | C | H | Cl | N | S |
|---|---|---|---|---|---|
| Calculated value (%) for $C_{10}H_{12}ClN_3O_5S$ | 37.33 | 3.76 | 11.02 | 13.06 | 9.97 |
| Found value (%) | 37.25 | 3.66 | 11.13 | 12.98 | 9.77 |

NMR spectrum ($\delta_{TMS}^{CDCl_3}$, ppm): 3.70 (2H, t, J=6 Hz), 3.92 (3H, s), 4.00 (3H, s), 4.46 (2H, t), 7.16 (1H, s), 10.00 (1H, br: disappeared when the spectrum was recorded in $D_2O$).

EXAMPLE 6

The procedure of Example 4 was repeated using chloroformic acid β,β,β-trichloroethyl ester. As a result, there was obtained a 77% yield of 2-[(2-β,β,β-trichloroethoxycarbonylamino)thiazol-4-yl]-2-syn-methoxyiminoacetic acid methyl ester (recrystallized from a mixture of chloroform and n-hexane).

Melting point: 119°–120° C.
Elemental analysis:

|  | C | H | Cl | N | S |
|---|---|---|---|---|---|
| Calculated value (%) for $C_{10}H_{10}Cl_3N_3O_5S$ | 30.75 | 2.58 | 27.23 | 10.76 | 8.21 |
| Found value (%) | 30.55 | 2.60 | 27.35 | 10.96 | 8.36 |

NMR spectrum ($\delta_{TMS}^{CDCl_3}$, PPM): 3.83 (3H, s), 4.02 (3H, s), 4.88 (2H, s), 7.24 (1H, s), 9.40 (1H, br: disappeared when the spectrum was recorded in $D_2O$).

EXAMPLE 7

The procedure of Example 4 was repeated using chloroformic acid ethyl ester. As a result, there was obtained a 52% yield of 2-[(2-ethoxycarbonylamino)-thiazol-4-yl]-2-syn-methoxyiminoacetic acid methyl ester.

Melting point: 126°–127° C.
Elemental analysis:

|  | C | H | N | S |
|---|---|---|---|---|
| Calculated value (%) for $C_{10}H_{13}N_3O_5S$ | 41.80 | 4.56 | 14.63 | 11.16 |
| Found value (%) | 41.71 | 4.60 | 14.59 | 11.11 |

NMR spectrum ($\delta_{TMS}^{CDCl_3}$, ppm): 1.3 (3H, t, J=7 Hz), 3.88 (3H, s); 3.94 (3H, s), 4.26 (2H, q, J=7 Hz), 7.12 (1H, s), 10.24 (1H, s: disappeared when the spectrum was recorded in $D_2O$).

EXAMPLE 8

A solution was prepared by dissolving 4.3 g of 2-(2-aminothiazol-4-yl)-2-syn-methoxyiminoacetic acid methyl ester in 40 ml of tetrahydrofuran and adding thereto 2.0 g of triethylamine, and then cooled to 5° C. or below. After 10 ml of toluene containing 0.99 g of phosgene was slowly added dropwise to the above solution, the resulting reaction mixture was stirred at room temperature for 5 hours. This reaction mixture was filtered to remove any insoluble matter. The filtrate was concentrated under reduced pressure and the resulting residue taken up in chloroform was washed with water. The crude product thus obtained was subjected to silica gel column chromatography, in which a yield of 2.6 g of N,N'-bis[4-syn-(carbomethoxy methoxyiminomethyl)thiazol-2-yl]urea was obtained by elution with a 40:1 mixture of chloroform and tetrahydrofuran.

Melting point: 130°–135° C.

Elemental analysis:

|  | C | H | N | S |
|---|---|---|---|---|
| Calculated value (%) for $C_{15}H_{16}N_6O_7S_2$ | 39.47 | 3.53 | 18.41 | 14.05 |
| Found value (%) | 39.33 | 3.49 | 18.69 | 14.11 |

NMR spectrum ($\delta_{TMS}^{CDCl_3}$, ppm): 3.86 (6H, s), 3.88 (6H, s), 7.10 (2H, s), 11.88 (2H, br: disappeared when the spectrum was recorded in $D_2O$).

EXAMPLE 9

A solution was prepared by dissolving 2.15 g of 2-(2-aminothiazol-4-yl)-2-syn-methoxyiminoacetic acid methyl ester in 30 ml of tetrahydrofuran and adding thereto 1.0 g of triethylamine, and then cooled to 0° C. After 0.64 g of oxalyl chloride was added to the above solution, the resulting reaction mixture was stirred at room temperature for 3 hours and then at reflux temperature for 1 hour. This reaction mixture was concentrated under reduced pressure and the resulting residue was washed successively with water, methyl alcohol, and tetrahydrofuran. The crude product thus obtained was then recrystallized from N,N-dimethylformamide to obtain a yield of 1.6 g of N,N'-bis[4-syn-(carbomethoxy methoxyiminomethyl)thiazol-2-yl]oxamide.

Melting point: 260°–262° C. (decomposed).

Elemental analysis:

|  | C | H | N | S |
|---|---|---|---|---|
| Calculated value (%) for $C_{16}H_{16}N_6O_8S_2$ | 39.67 | 3.33 | 17.35 | 13.24 |
| Found value (%) | 39.70 | 3.30 | 17.34 | 12.99 |

NMR spectrum ($\delta_{TMS}^{DMSO-d_6}$, ppm): 3.9 (6H, s), b 3.98 (6H, s), 7.78 (2H, s), 13.38 (2H, s: disappeared when the spectrum was recorded in $D_2O$).

We claim:

1. Method for treating a patient suffering from an immunodisease which comprises administering to said patient an effective immunodulating amount of 2-thiazolamine derivative of the formula:

$$R_1OOC-C \underset{\underset{R_2O}{\diagdown}N}{\overset{\phantom{x}}{\|}} \overset{N}{\underset{S}{\diagup}} \overset{\|}{\diagdown} NHCO-X \quad (1)$$

wherein $R_1$ and $R_2$ independently are each a lower alkyl radical having 1 to 4 carbon atoms and X is a lower alkyl radical, a lower alkoxy radical or a haloalkoxy radical, and a member of the group consisting of (i) a pharmaceutically acceptable diluent, (ii) a pharmaceutically acceptable carrier and (iii) a combination of (i) and (ii).

2. The method for treating a patient suffering an immunodisease as claimed in claim 1 wherein the compound of formula (1) is 2-[(2-propionylamino)thiazol-4-yl]-2-syn-methoxyiminoacetic acid methyl ester.

3. The method for treating a patient suffering from an immunodisease as claimed in claim 1 wherein the compound of formula (1) is 2-[2-β-chloroethoxycarbonylamino)thiazol-4-yl]-2-syn-methoxyiminoacetic acid methyl ester.

4. The method for treating a patient suffering an immunodisease as claimed in claim 1 wherein the compound of formula (1) is 2-[(2-β,β,β-trichloroethoxycarbonylamino)thiazol-4-yl]-2-syn-methoxyiminoacetic acid methyl ester.

5. The method for treating a patient suffering an immunodisease as claimed in formula (1) is 2-[(2-ethoxycarbonylamino)thiazol-4-yl]-2-syn-methoxyiminoacetic acid methyl ester.

6. The method for treating a patient suffering from an immunodisease as claimed in claim 1 wherein said immunodisease is rheumatoid arthritis.

* * * * *